United States Patent [19]
Yoshizo et al.

[11] Patent Number: 5,471,261
[45] Date of Patent: Nov. 28, 1995

[54] APPARATUS FOR OBTAINING IMAGES OF CORNEA ENDOTHELIUM

[75] Inventors: Ikegami Yoshizo; Kuniomi Abe; Masahiko Konagaya, all of Nishinomiya, Japan

[73] Assignee: Konan Inc., Hyogo, Japan

[21] Appl. No.: 296,031

[22] Filed: Aug. 25, 1994

[30]     Foreign Application Priority Data

Sep. 2, 1993  [JP]  Japan .................................... 5-241986
Nov. 30, 1993  [JP]  Japan .................................... 5-329658

[51] Int. Cl.⁶ ...................................................... A61B 3/14
[52] U.S. Cl. .......................... 351/210; 351/209; 351/211; 351/214
[58] Field of Search ..................................... 351/206, 214, 351/212, 247, 221, 205, 211, 209, 210

[56]             References Cited
              U.S. PATENT DOCUMENTS 5,381,194   1/1995   Nishio et al. ........................... 351/206

Primary Examiner—William L. Sikes
Assistant Examiner—Hung Xuan Dang
Attorney, Agent, or Firm—Koda and Androlia

[57]                ABSTRACT

An apparatus for obtaining images of cornea endothelium including an illumination system for illuminating through a slit an eyeball surface of a subject eye, a magnification-imaging optical system for forming a magnified image of a subject part based on the slit illumination light, focusing-detection use receiving optics for receiving the cornea endothelium reflected light and cornea epithelium reflected light of the slit via at least an objective lens when a cornea endothelium image is formed on an imaging surface of the magnification-imaging optical system in a focused state and a mechanism for moving the apparatus body in a direction of the subject so that the apparatus body is brought to a cornea endothelium focused position.

10 Claims, 7 Drawing Sheets

Z-AXIS DIRECTION

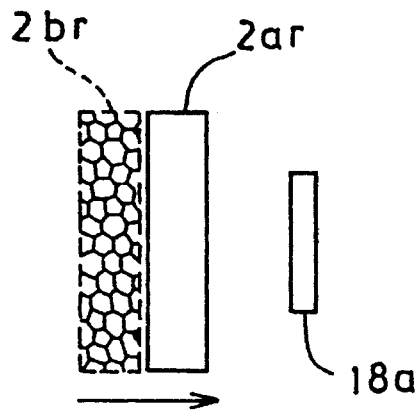
FIG.5(a) REFLECTED CORNEA IMAGE IN IMAGE-FORMING
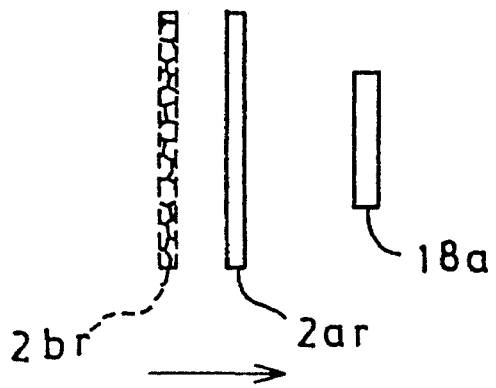
FIG.5(b) REFLECTED CORNEA IMAGE IN FOCUS DETECTION
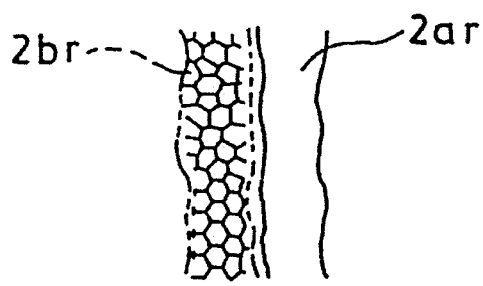
FIG.6

APPARATUS FOR OBTAINING IMAGES OF CORNEA ENDOTHELIUM

BACKGROUND OF THE INVENTION

1. Field of the Invention

The present invention relates to an apparatus for obtaining images of cornea endothelium, by which images of cornea endothelium cells of an eyeball of a subject person can be observed or photographed under magnification. More specifically, the invention relates to an apparatus for obtaining images of cornea endothelium, which apparatus is capable of detecting a cornea endothelium focused position by detecting weak cornea-endothelium reflected light with high accuracy and reliability, and also relates to an apparatus for obtaining images of cornea endothelium, which apparatus is capable of measuring cornea thickness with high accuracy by detecting epithelium reflected light with high accuracy.

For seeing influences of contact lenses or for medical examination and treatment before and after an operation of cataract, it is necessary to observe the state of cornea endothelium cells. Therefore, for observing or photographing under magnification cornea endothelium cells of an eyeball of a subject person, there have conventionally been used apparatus in which with an objective lens of a microscope of non-contact type or contact type with respect to the eyeball surface of the subject person, slit illumination light is applied toward an observation part obliquely of the eye axis, and its reflected light from the cornea is magnified, in which state the cornea endothelium cells can be observed, or in which apparatus an optimum imaging position where a TV camera or the like is focused on cornea endothelium is detected by the principle of the so-called triangulation method by detecting the position of the reflected light of the slit illumination light from the cornea endothelium, in which state the cornea endothelium cells of the subject part can be imaged by the TV camera or the like.

To solve these inconveniences in operation of the conventional apparatus, the present applicant has previously proposed an apparatus which is capable of automatically observing or photographing under magnification images of cornea endothelium cells of a subject part and moreover which is capable of measuring cornea thickness of the subject eye besides the observation and photographing under magnification, in Japanese Patent Application No. HEI 05-166132, filed Jun. 10, 1993. In this apparatus, for measurement of cornea thickness, one light receiving element has been used to detect two rays of reflected light from cornea epithelium and cornea endothelium.

However, in these conventional apparatus, the focusing on the cornea endothelium has been accomplished by manually moving a microscope frame, on which a TV camera is mounted, back and forth with the use of an operation member such as a joy stick. In this operation, since epithelium reflection is intense and endothelium reflection is weak with a large difference therebetween when the subject part is illuminated through a slit and the resulting cornea reflected light is used to obtain a focusing, it has been difficult to detect endothelium reflected light and therefore difficult to accomplish the focusing on the cornea endothelium, as a problem. As a result, considerable labors and skills would be needed to accomplish the focusing on the cornea endothelium cells of the subject part.

Another problem is that it has been difficult to detect both epithelium reflected light and endothelium reflected light reliably and correctly. Further, for measurement of the cornea thickness, there has still been a demand of accurately detecting epithelium reflection as well as endothelium reflection.

SUMMARY OF THE INVENTION

The present invention has been achieved in view of the above-described problems. Accordingly, a principal object of the present invention is to provide an apparatus capable of observing and photographing under magnification cornea endothelium cells of a subject part by detecting an optimum imaging position based on such an arrangement that the apparatus can easily and reliably detect endothelium reflected light, which is substantially weaker than epithelium reflected light, in illuminating through a slit the eyeball surface of a subject eye and accomplishing the focusing of cornea reflected light. Another object of the present invention is to provide an apparatus for obtaining images of cornea endothelium, which is capable of detecting epithelium reflection with high accuracy and measuring cornea thickness with simplicity and reliability.

To achieve the above objects, the present invention provides an apparatus for obtaining images of cornea endothelium, which comprises an illumination system for illuminating through a slit an eyeball surface of a subject eye, a magnification-imaging optical system for forming a magnified image of a subject part based on slit illumination light with which the eyeball surface has been illuminated, focusing-detection use receiving optics set in such a position as to receive cornea endothelium reflected light or cornea epithelium reflected light of the slit light via at least an objective lens when a cornea endothelium image is formed on an imaging surface of the magnification-imaging optical system in a focused state, and a means for moving the apparatus body in the direction of the subject eye so that the apparatus body is brought to a cornea endothelium focused position, wherein the focusing-detection use receiving optics includes a slit-light-received-state control means for enhancing detectability of the cornea endothelium reflected light.

Advantageously, the light-received-state control means included in the focusing-detection use receiving optics may be a slitted aperture elongated in the longitudinal direction of a cornea reflected image resulting from the slit illumination light, the slitted aperture being arranged forward of the focusing-detection use receiving optics.

Also, effectively, the light-received-state control means included in the focusing-detection use receiving optics may control to increase the quantity of slit illumination light of the illumination system by an epithelium reflected light detection signal that is first detected by the focusing-detection use receiving optics, or may control to increase photoreception sensitivity of the focusing-detection use receiving optics similarly by the epithelium reflected light detection signal so that the detectability of cornea endothelium reflected light can be enhanced.

Also, the light-received-state control means included in the focusing-detection use receiving optics may be an optical system for compressing the longitudinal direction of a cornea reflected image resulting from the slit illumination light, the optical system being arranged forward of the focusing-detection use receiving optics.

Further, advantageously, the light-received-state control means included in the focusing-detection use receiving optics may be a detection-use slitted aperture which is provided independently of an imaging-use slitted aperture in the slit illumination system and which is smaller in width than the imaging-use slitted aperture.

The present invention provides another apparatus for obtaining images of cornea endothelium, which comprises an illumination system for illuminating through a slit an eyeball surface of a subject eye, a magnification-imaging optical system for forming a magnified image of a subject part based on slit illumination light with which the eyeball surface has been illuminated, focusing-detection use receiving optics set in such a position as to receive cornea endothelium reflected light or cornea epithelium reflected light of the slit light via at least an objective lens when a cornea endothelium image is formed on an imaging surface of the magnification-imaging optical system in a focused state, and a means for moving the apparatus body in the direction of the subject eye so that the apparatus body is brought to a cornea endothelium focused position, wherein the focusing-detection use receiving optics comprises two light receiving elements of a photoreceptor for receiving cornea endothelium reflected light and a photoreceptor for receiving cornea epithelium reflected light.

Advantageously, in the apparatus for obtaining images of cornea endothelium, the photoreceptor for receiving cornea epithelium reflected light may be a light receiving element capable of detecting an extent of movement of the epithelium reflected light in its moving direction, wherein cornea thickness is calculated in correspondence to an epithelium-reflected-light received position on the photoreceptor for receiving the cornea epithelium reflected light at the time when the photoreceptor for receiving the cornea endothelium reflected light has detected the endothelium reflected light.

In the apparatus for obtaining images of cornea endothelium according to a first aspect of the present invention, a magnified image of endothelium of a subject part is formed by the magnification-imaging optical system based on reflected light from the eyeball surface illuminated through a slit by the illumination system. In this process, as shown in FIG. 2, which is a view of the principle of focusing on cornea by the receiving optics with the use of the so-called triangulation method, when the imaging system is manually or automatically moved forth toward the subject eye with the result of a relative movement Em between the imaging system and the subject eye, a ray of slit illumination light elongated in vertical direction and projected onto a cornea 2 of a subject person through a projection lens 13 from an illumination optical axis 12 is reflected at a reflective spot 2ar' on a cornea epithelium 2a surface so that slitted epithelium reflected light 2ar moves via an objective lens 15 in the direction of arrow Crm representing the movement of cornea reflected light, while a ray of illumination light that has passed through the epithelium is reflected at a reflective spot 2br' on a cornea endothelium 2b surface on the illumination optical axis 12 so that slitted endothelium reflected light 2br moves also via the objective lens 15 in the direction of Crm in succession to the slitted epithelium reflected light 2ar in an adjacent state (with a small gap).

Then, when the endothelium reflected light 2br (or the epithelium reflected light 2ar) is incident on receiving optics 18 set in a position where the endothelium reflected light 2br (or the epithelium reflected light 2ar) will be located when a cornea endothelium image is formed on an image receiving surface (CCD photoreceptive surface; see FIG. 1) 22 of a TV camera 23 in a focused state, the cornea endothelium of the subject eye is focused on the photoreceptive surface of the TV camera, in which state a magnified image of cornea endothelium cells can be observed or photographed via an unshown monitor from the TV camera 23.

For detection of the imaging position in this apparatus, when cornea endothelium reflected light is detected by the focusing-detection use receiving optics 18, the epithelium reflected light 2ar and successively the endothelium reflected light 2br travel across the front of receiving optics 18 as the imaging system moves forth, as it is viewed from arrow C, so that photoreception signals of epithelium reflection and endothelium reflection are obtained from the receiving optics 18. In this process, if a slitted aperture elongated in the longitudinal direction of the cornea reflected image resulting from the slit illumination light is arranged in front of the focusing-detection use receiving optics 18, the endothelium reflection substantially weaker than the epithelium reflection will show clearer peaks as shown in FIG. 3, compared with the case where no slitted aperture is provided in front of the receiving optics. Thus, the endothelium reflection can be better separated from the proximate epithelium reflection, so that cornea endothelium reflected light can be detected with reliability.

Also, for the focusing-detection use receiving optics 18 to detect the endothelium reflected light 2br in succession to the epithelium reflected light 2ar, it is possible that the rising edge of the brighter endothelium-reflected-light reception signal, which is to be detected earlier by the receiving optics 18, is captured and this is used as a trigger for switching to boost the illumination lamp voltage or for opening the aperture within the illumination optical system or for other operation so that the quantity of slit illumination light is increased for more brightness or that the gain of the amplifier of the receiving optics 18 is switched over. Then, the gain of the endothelium-reflected-light reception signal in the receiving optics 18 can be increased (see FIG. 4), whereby the cornea endothelium reflected light can be detected with reliability.

It is also possible that an optical system (e.g., cylindrical lens) for compressing the longitudinal direction of a cornea reflected image resulting from slit illumination light is arranged in front of the focusing-detection use receiving optics 18. Then, the slitted cornea reflected image can be received on the whole by the receiving optics without waste, so that the detectability of the receiving optics 18 for cornea endothelium reflected light can be enhanced.

Further, if an imaging-position detection use slitted aperture independent of an imaging-use slitted aperture and smaller in width than the image-use slitted aperture is used in the slit illumination optical system, a slitted aperture smaller in width than the conventional slitted aperture that serves for both imaging and detection use can be used for use of detection of an imaging position. In this case, when an image is obtained by illumination with imaging-use slit light as shown in FIGS. 5A and 5B representing the relation between receiving optics and cornea reflected light as viewed in the direction of arrow C in FIG. 2, rays of cornea reflected light 2ar, 2br substantially larger in width than a photoreceptive area 18a of the receiving optics that has been narrowed by the slitted aperture can be obtained so that a field of view wider than has been conventionally can be used for imaging. Moreover, when an image is obtained by illumination with the detection-use slit light, rays of cornea reflected light 2ar, 2br rather smaller in width than the aforementioned photoreceptive area 18a of the receiving optics can be obtained so that cornea endothelium reflection can be detected with higher accuracy than has been conventionally, to detect the imaging position. In addition, the arrow in FIG. 5 shows the direction in which the cornea reflected light 2ar, 2br moves as the imaging system is moved forth toward the subject eye. The image of cornea epithelium reflected light $2ar$ and the image of cornea endothelium reflected light $2br$ in FIG. 5, although actually having unclear profiles due to reflection from a living body as shown in FIG. 6, are illustrated in simplified form in FIG. 5 for explanation's sake.

In the apparatus for obtaining images of cornea endothelium according to another aspect of the present invention, a magnified image of cornea endothelium of a subject part is formed by the magnification-imaging optical system based on reflected light from the eyeball surface illuminated through a slit by the illumination system. In this case, as shown in the optical path diagram of the apparatus for obtaining images of cornea endothelium in FIG. 7, when the imaging system 3 is manually or automatically moved forth toward the subject eye with the result of a relative movement between the imaging system 3 and the subject eye, a vertically elongated ray of slit illumination light projected from the illumination lamp 4 onto the cornea 2 through the illumination system is reflected by the epithelium surface of the cornea 2 so that slitted epithelium reflected light moves in front of an endothelium-focusing detection use receiving optics $18_1$ via the objective lens 15, while the illumination light that has passed the cornea epithelium is reflected by a cornea endothelium surface deeper than the cornea epithelium surface on the illumination optical axis 12 so that slitted endothelium reflected light moves in front of the endothelium-focusing detection use receiving optics $18_1$ in succession to the slitted epithelium reflected light with a small gap in an adjacent state, also via the objective lens 15.

As for an epithelium-focusing detection use receiving optics $18_2$ located on another optical axis $14_2$ of the magnification-imaging optical system independently of the endothelium-focusing detection use receiving optics $18_1$, endothelium reflected light moves in front of the epithelium-focusing detection use receiving optics $18_2$ in succession to the epithelium reflected light as in the above case. Then, when the endothelium reflected light of the cornea reflected light that moves in front of the receiving optics $18_1$ is incident on the photoreceptive area of the receiving optics $18_1$ so that an endothelium-focused state is detected, a magnified image of cornea endothelium of the subject part is focused on the image receiving surface 22 of the TV camera 23. Thus, the strobe discharge tube 8 of the illumination system emits light, so that a magnified image of cornea endothelium cells can be observed or photographed via a monitor 33 from the TV camera 23 (see FIG. 8). In this case, if a photoreceptor optimum for detection of endothelium reflected light (e.g., phototransistor) is used as the endothelium-focusing detection use receiving optics $18_1$ and a photoreceptor optimum for detection of epithelium reflected light (e.g., line sensor, PSD, or the like) is used as the epithelium-focusing detection use receiving optics $18_2$, then a variety of modifications may be devised in their photoreceptive optical paths according to applications without care for interaction between the two photoreceptors, so that an increased degree of freedom of design makes it easy to control the photoreceptive function. As a result, the detection of endothelium can be accomplished with simplicity and accuracy, and moreover the position of epithelium at the time when the endothelium is detected can be detected with high accuracy.

Further, if a photoreceptor that can detect the extent of movement of cornea epithelium reflected light in its moving direction is used as the receiving optics $18_2$ that receives cornea epithelium reflected light and if cornea thickness is calculated in correspondence to the epithelium-reflected-light received position on the receiving optics $18_2$ at the time when the endothelium reflected light is detected by the receiving optics $18_1$ that receives cornea endothelium reflected light, then measurement of cornea thickness can be easily accomplished in electronic fashion without using a mechanical encoder, which is a moving-extent detection means and which was involved in the previous patent application (Japanese Patent Application No. HEI 05-166132). It is also allowable to use an imaging-use CCD camera as the receiving optics $18_2$.

BRIEF DESCRIPTION OF THE DRAWINGS

FIGS. 5A and 5D are a schematic view showing the relation between the photoreceptive area of the receiving optics and cornea reflected light at the time when the detection- and imaging-use apertures of the slit illumination optical system are changed;

FIG. 6 is a view of actual cornea reflected light in obtaining an image;

DETAILED DESCRIPTION OF THE PREFERRED EMBODIMENTS

Embodiments of the present invention are now described with reference to the accompanying drawings.

(Embodiment 1)

Figure 1:
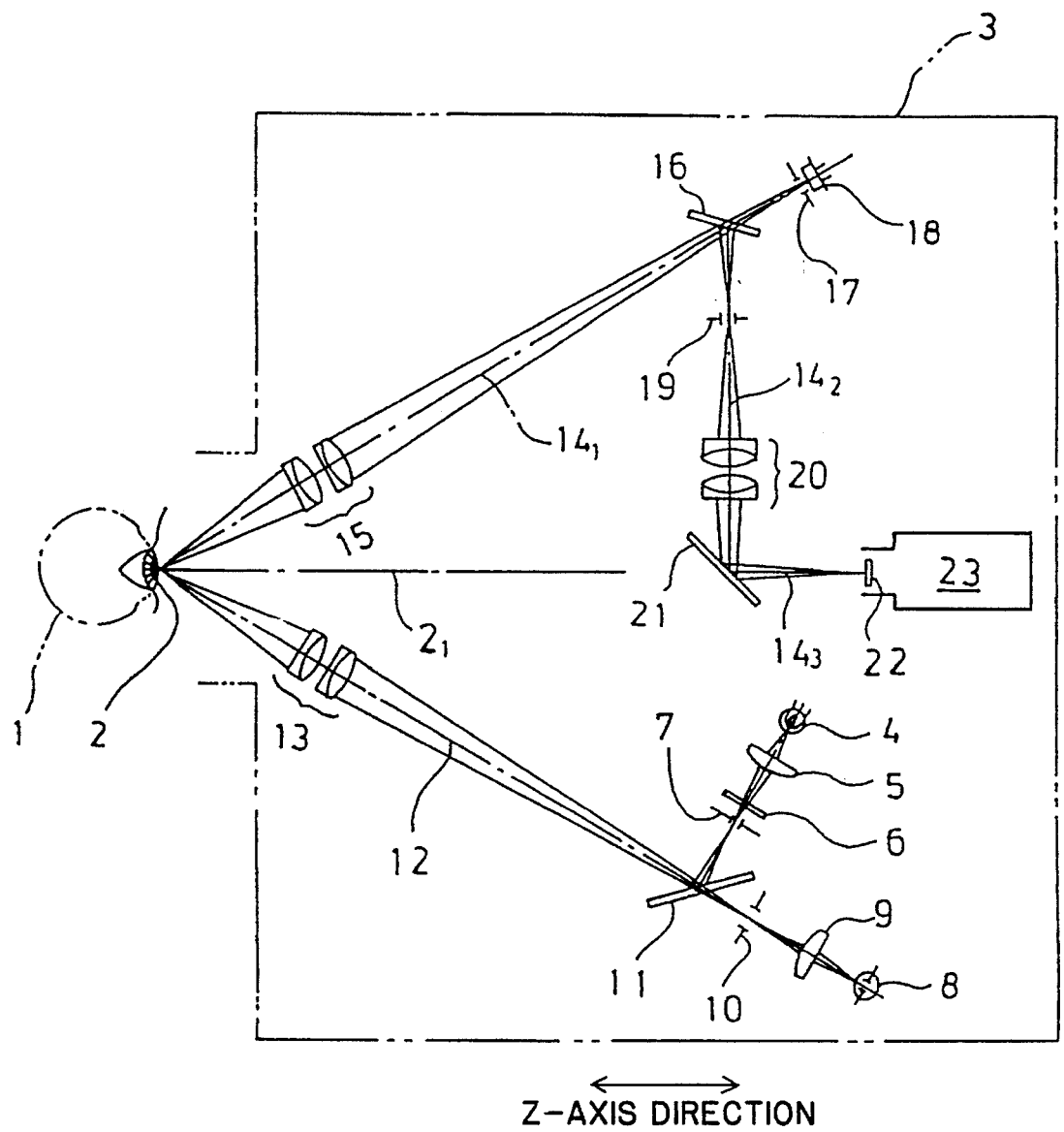
FIG. 1 is an optical path diagram of a first embodiment of the present invention.
Figure 2:
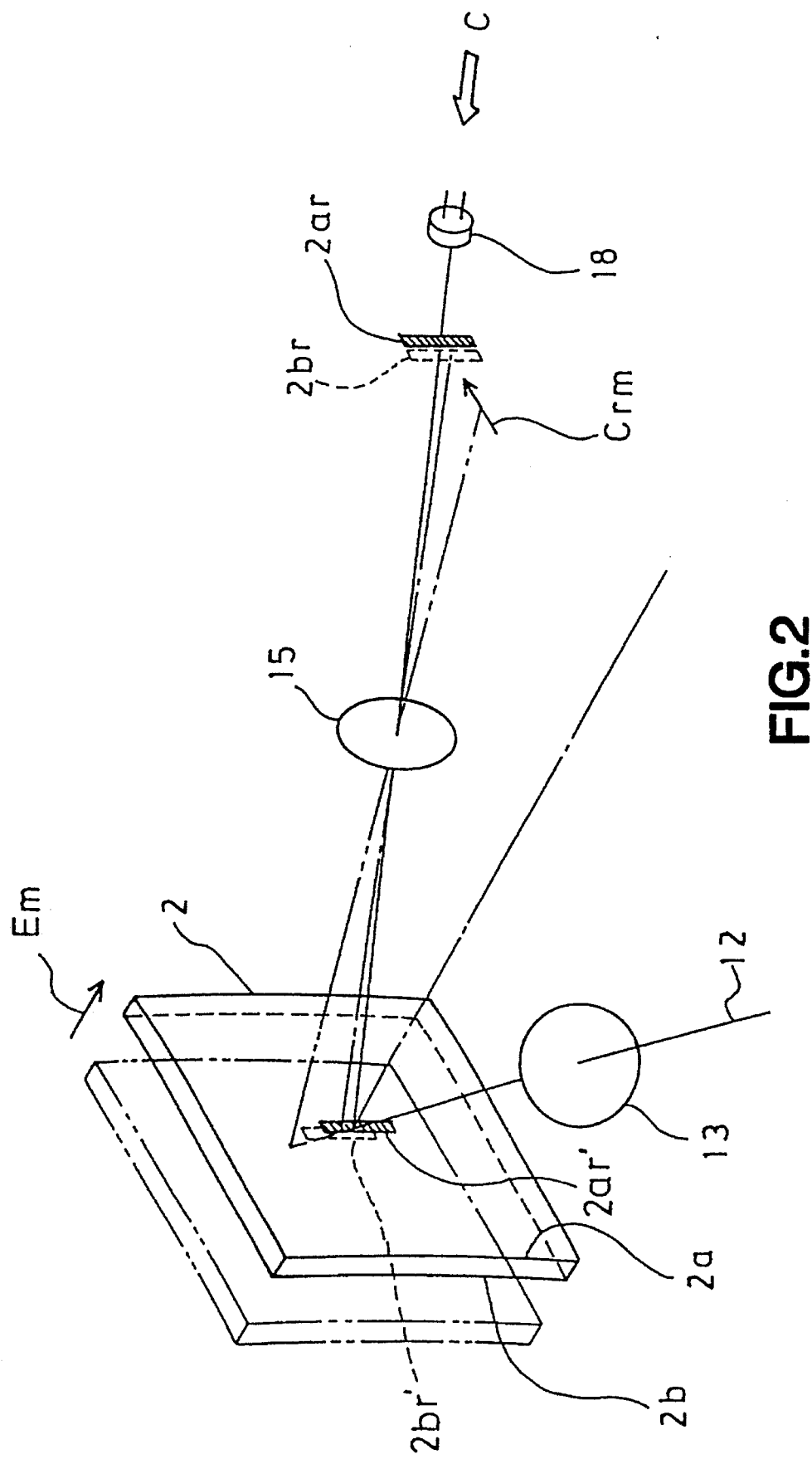
FIG. 2 is a perspective view showing the principle of focusing in FIG. 1.

FIG. 1 is an optical path diagram of the present embodiment.

In FIG. 1, there is shown an imaging system 3 comprising an illumination system for illuminating through a slit an eyeball surface 2 of a subject eye 1, and a magnification-imaging optical system which faces the eyeball surface 2 and which is capable of observing or photographing under magnification an image of the subject part by a TV camera 23 based on slit illumination light with which the eyeball surface has been illuminated, the imaging system 3 further comprising focusing-detection use receiving optics 18 for detecting an optimum imaging position by detecting cornea endothelium reflection (or cornea epithelium reflection) of the subject part with the optical path of the magnification-imaging optical system partly extended. The imaging system 3 is moved by an unshown Z-axis drive mechanism in the direction of the eye axis of the subject eye 1.

As illumination sources for the subject part of the eyeball surface 2, there are provided an illumination lamp 4 used for focusing of the magnification-imaging optical system and a strobe discharge tube 8 used for photographing cornea endothelium cells under magnification. In order that rays of light emitted by the respective illumination sources illuminate the cornea 2, which is an observation surface of the subject eye 1, from an illumination optical axis 12 via a projection lens 13 at a specified angle obliquely with respect to the eye axis, the strobe discharge tube 8 is located in a specified position on the illumination optical axis 12 while the illumination lamp 4 is located on an optical axis perpendicular to the illumination optical axis 12 via a half mirror 11 on the illumination optical axis 12.

Further, for the light emitted by the illumination lamp 4, at a position where it is focused by a condenser lens 5 there is provided a detection-use slit aperture 7 having a specified small width and corresponding to a slit aperture 17 in front of later-described focusing-detection use receiving optics 18. Meanwhile, for the light emitted by the strobe discharge tube 8, at a position where it is focused by a condenser lens 9 there is provided an imaging-use slit aperture 10 having a specified rather large width and being purposed for allowing a wider view field imaging, in which case a visible-light cut filter 6 is further provided on the optical axis of the illumination lamp 4 forward of the detection-use slit aperture 7. Thus, only infrared light out of the light of the illumination lamp 4 is reflected by the half mirror 11, which reflects infrared light and transmits visible light, and projected onto the cornea 2, while visible light of the strobe discharge tube 8 is transmitted by the half mirror 11 and projected onto the eyeball surface 2.

Also, on the side opposite to the illumination optical axis 12 of the illumination system with the eye axis $2_1$ of the subject eye interposed therebetween, there is provided a magnification-imaging optical system which, receiving cornea-reflected light of the oblique slitted illumination light from the illumination lamp 4 or the strobe discharge tube 8 to the eyeball surface 2, forms an image of cornea endothelium cells of the subject part on an image receiving surface (CCD photoreceptive surface) 22 of the TV camera 23, thus allowing the image of the cornea endothelium cells to be observed or photographed under magnification. When the cornea endothelium image is formed on the image receiving surface 22 of the TV camera 23 in a focused state, the focusing-detection use receiving optics 18 set in a position resulting from partly extending the optical path of the optical system detects cornea endothelium reflected light (or cornea epithelium reflected light) that moves in front of the receiving optics as the imaging system 3 moves forward.

Figure 3:
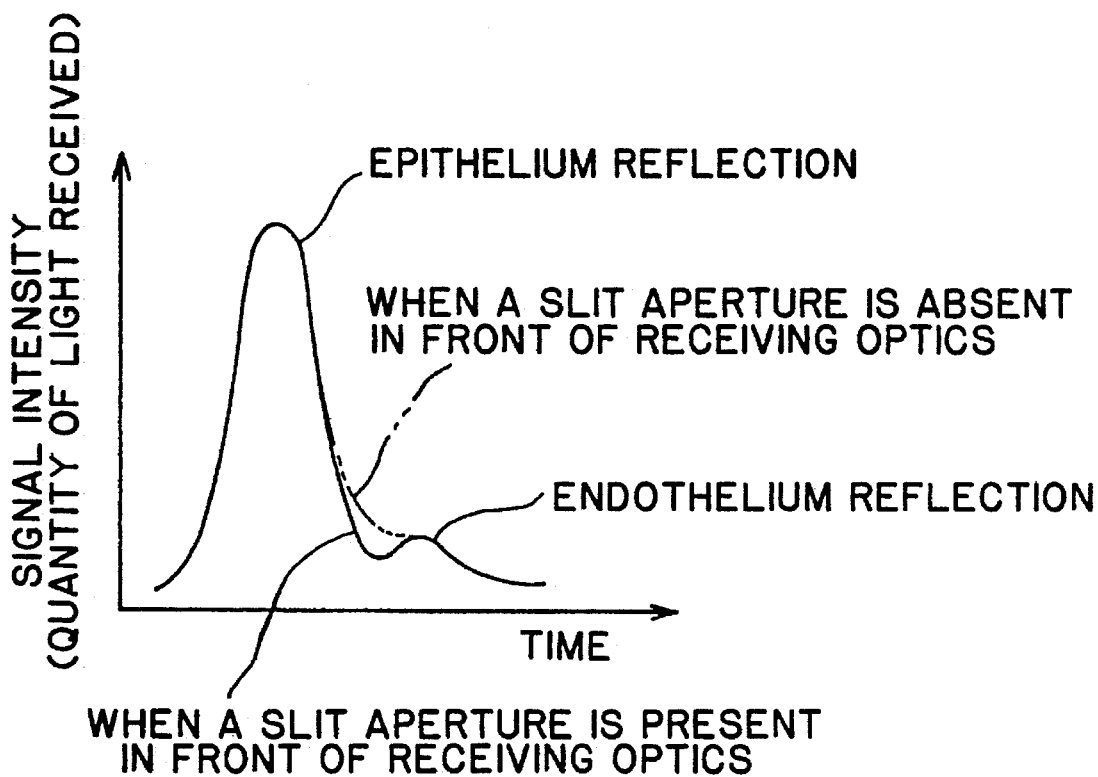
FIG. 3 is a curve chart showing how epithelium reflection and endothelium reflection are separated from each other depending on whether the slitted aperture in front of the receiving optics is present or absent.
Figure 4:
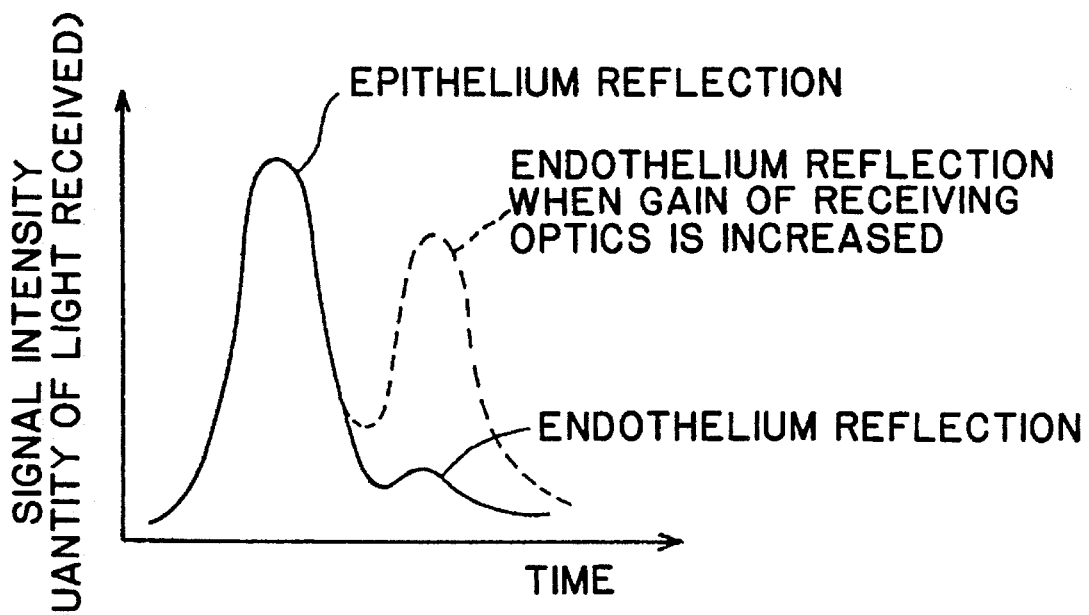
FIG. 4 is a curve chart of the photoreception signal resulting when the receiving optics is increased in gain at the rising edge of an epithelium-reflected-light reception signal in the receiving optics.

In more detail, at specified positions on an optical axis $14_1$ of the magnification-imaging optical system located symmetrically with the illumination optical axis 12 of the illumination system with respect to the eye axis $2_1$ of the subject eye 1, an objective lens 15 is disposed on the eyeball surface side and a half mirror 16, which transmits infrared light and reflects visible light, is disposed at a specified distance from the objective lens 15, so as to cross the optical axis $14_1$ at a specified angle and thereby to bend an image ray of reflected light of the above illumination light derived from the eyeball surface so that the image ray will orthogonally cross the axis line of the eye axis $2_1$ at a specified position generally on the axis line. The image ray reflected by the half mirror 16 passes on the optical axis $14_2$ through a field diaphragm 19 and a magnifying lens 20, which are located on an intermediate image-forming plane. Then, visible light of imaging-use slit light by the strobe light out of the magnified image ray is totally reflected by a mirror 21 crossing the eye axis $2_1$ at 45°, so as to be incident on the image receiving surface (CCD photoreceptive surface) 22 of the TV camera 23 provided on a bent optical axis $14_3$. Meanwhile, infrared light of the imaging-position detection use slit light is incident on the focusing-detection use receiving optics 18 provided at a position where the image of the cornea reflected image ray is formed by the objective lens 15, the position resulting from extending the optical path on the optical axis $14_1$. Then, when the cornea endothelium image is formed on the image receiving surface 22 of the TV camera 23 by the objective lens 15 and the magnifying lens 20 in a focused state, slitted endothelium reflected light is incident as it is better separated from adjacent epithelium reflection by the slit aperture 17 elongated in the longitudinal direction of the cornea reflected image in front of the focusing-detection use receiving optics 18 (see FIG. 3). At the same time, by detection-use slit light that is incident on the photoreceptive area 18a of the receiving optics 18 as it is reduced in width by the slit aperture 7 located at the position where the light emitted by the illumination lamp 4 is focused (see FIG. 5), cornea endothelium reflected light can be detected by the receiving optics 18 with high positional accuracy and reliability, so that an optimum imaging position for the apparatus can be detected.

In the above process, it is possible that the quantity of slit illumination light is increased by switching to boost the voltage of the illumination lamp 4 at the rising edge of the epithelium-reflected-light reception signal that comes first from the focusing-detection use receiving optics 18, whereby endothelium reflected light that is too dark to detect is brightened until the difference in intensity between epithelium reflection and endothelium reflection is eliminated so that the endothelium reflected light can be detected with reliability. Further, it is also possible that the gain of the amplifier of the receiving optics 18 is switched over also at the rising edge of the epithelium-reflected-light reception signal, whereby the sensitivity of the receiving optics is enhanced so that endothelium reflected light can be detected with reliability. Furthermore, it is also possible that a cylindrical lens is disposed in front of the receiving optics 18 so that a slitted reflected image of cornea is received on the whole by the receiving optics without waste, in which case cornea endothelium reflection can be detected with efficiency. Thus, the state of slit light reception by the focusing-detection use receiving optics may be controlled by using various means so that detectability of cornea endothelium reflected light can be enhanced and therefore cornea endothelium reflected light can be detected with reliability for detection of an optimum imaging position for the apparatus.

For the setting of the imaging system 3 to the optimum imaging position, i.e., for focusing a cornea endothelium image on the image receiving surface 22 of the TV camera 23, the frame, on which the imaging system 3 is mounted, may be moved toward the subject eye by using an operation member such as a joy stick for manual operation, in which case the setting of the apparatus to an optimum imaging position can be easily accomplished by an indicator lamp or a beeper with a focusing signal from the focusing-detection use receiving optics 18. Moreover, the frame having the imaging system 3 mounted thereon may be moved forward from its standby position toward the subject eye with an arbitrary signal such as a signal representing that alignment light has entered a specified region of an eye-front image with an unshown eye-front imaging apparatus, in which case after the focusing-detection use receiving optics has detected epithelium reflection and when it detects endothelium reflection, the frame is stopped moving forward so that the optimum imaging position can be detected automatically.

(Embodiment 2)

As a second embodiment of the present invention, here described is a case in which both cornea endothelium reflected light and cornea epithelium reflected light can be detected with high accuracy, whereby cornea thickness is calculated and displayed in addition to the imaging of cornea endothelium.

Figure 7:
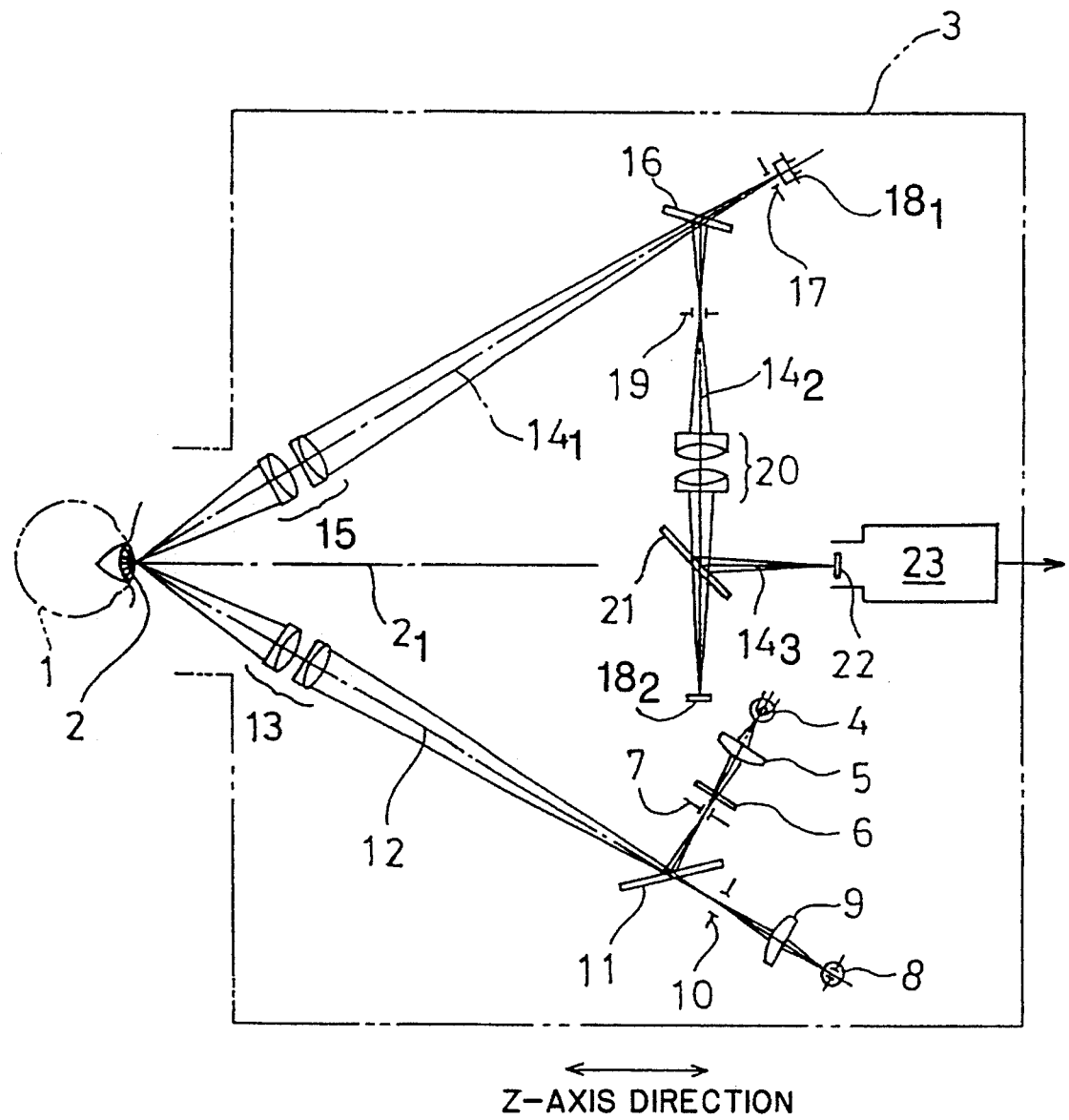
FIG. 7 is an optical path diagram of a second embodiment of the present invention.
Figure 8:
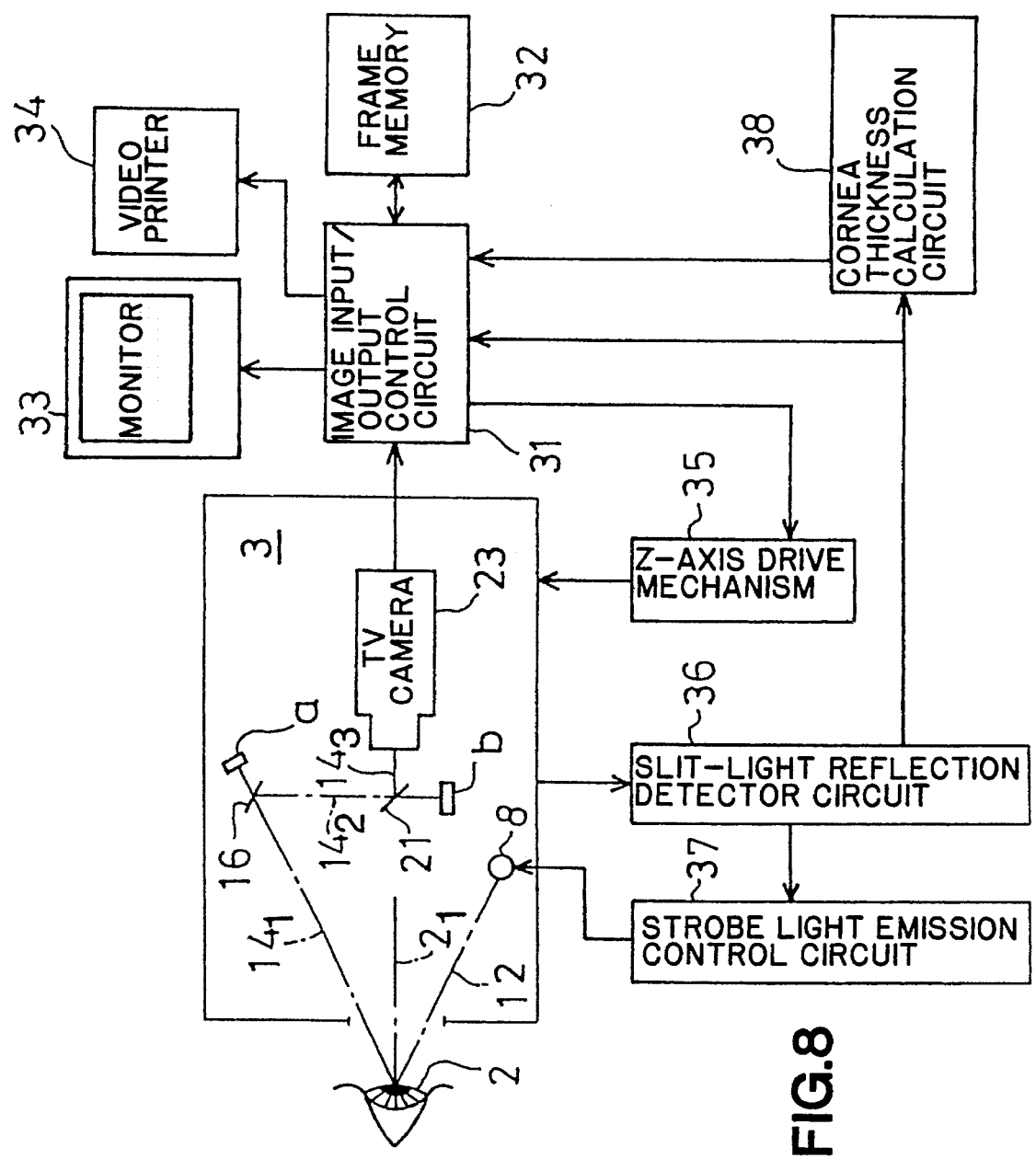
FIG. 8 is a block diagram of the second embodiment of the present invention.
Figure 9:
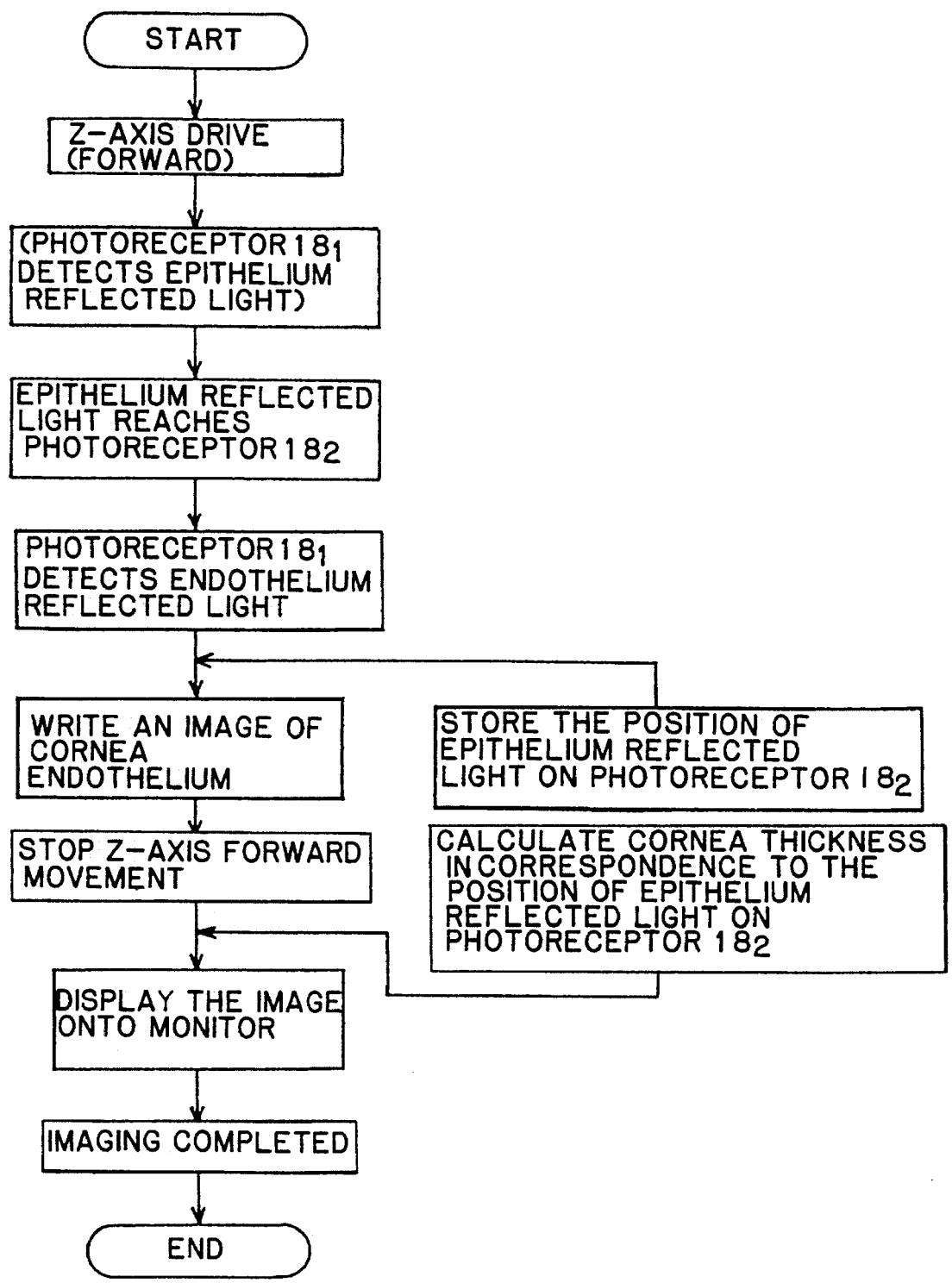
FIG. 9 is a flow Chart showing the procedure for the imaging of cornea endothelium and the calculation of cornea thickness.

FIG. 7 is an optical path diagram of the present embodiment. In this embodiment, the focusing-detection use receiving optics in the first embodiment is replaced with two photoreceptors, one for receiving cornea endothelium reflected light and the other for receiving cornea epithelium reflected light, so that each reflected light can be detected with high accuracy and thereby cornea thickness is calculated. FIG. 8 is a block diagram of the electric circuit of the present embodiment, and FIG. 9 is a flow chart showing the procedure for imaging the cornea endothelium and calculating the cornea thickness.

In FIG. 7, there is shown an imaging system 3 comprising an illumination system for illuminating through a slit an eyeball surface 2 of a subject eye 1, and a magnification-imaging optical system which faces the eyeball surface 2 and which is capable of observing or photographing under magnification an image of the subject part by a TV camera 23 based on slit illumination light with which the eyeball surface has been illuminated, the imaging system 3 further comprising a cornea-endothelium focusing-detection use receiving optics $18_1$ for detecting an optimum imaging position by detecting cornea endothelium reflection light of the subject part with an extended part $14_1$ of the optical path of the magnification-imaging optical system, and a cornea-epithelium focusing-detection use receiving optics $18_2$ for detecting the focusing of epithelium reflected light. The cornea-epithelium focusing-detection use receiving optics $18_2$ is so arranged as to have its photoreceptive surface at a position conjugate with the image receiving surface 22 of the TV camera with respect to the reflection surface of an infrared-light transmitting and visible-light reflecting half mirror 21' disposed to cross an optical axis $14_2$ at 45° on the optical axis $14_2$ branched from the optical axis $14_1$ of the magnification-imaging optical system. The cornea-epithelium focusing-detection use receiving optics $18_2$ is also so formed as to be able to detect the extent of movement of epithelium reflected light in its moving direction by its photoreceptive surface elongated in the direction in which slit reflected light moves.

The imaging system 3, which comprises the illumination system and the magnification-imaging optical system and which is further provided with the cornea-endothelium focusing-detection use receiving optics $18_1$ and the cornea-epithelium focusing-detection use receiving optics $18_2$, is moved by a later-described Z-axis drive mechanism 35 in the direction of the eye axis of the subject eye 1.

The arrangement of the illumination lamp 4 and the strobe discharge tube 8, which are illumination sources for the subject part of the eyeball surface 2, and the arrangement of the condenser lenses 5, 9, the detection-use slit aperture 7 of a specified small width, the imaging-use slit aperture 10 of a specified rather large width, the visible-light cut filter 6 before the detection-use slit aperture 7, the (visible-light transmitting and infrared-light reflecting ) half mirror 11, the projection lens 13, and the like are the same as in the first embodiment. The cornea 2, which is the observation surface of an eyeball 1 of a subject person, is illuminated through the projection lens 13 obliquely at a specified angle with respect to the eye axis from on the illumination optical axis 12 with illumination light by the illumination lamp 4 for focusing by the magnification-imaging optical system, and with strobe light by the strobe discharge tube 8 for imaging cornea cells under magnification.

Also, on the side opposite to the illumination optical axis 12 of the illumination system with the eye axis $2_1$ of the subject eye interposed therebetween, there is provided a magnification-imaging optical system which, receiving reflected light from the cornea 2 of the oblique slit illumination light from the illumination lamp 4 or the strobe discharge tube 8 to the eyeball surface 2, forms an image of cornea endothelium cells of the subject part on an image receiving surface (CCD photoreceptive surface) 22 of the TV camera 23, thus allowing an image of the cornea endothelium cells to be observed or photographed under magnification. When the cornea endothelium image is formed on the image receiving surface 22 of the TV camera 23 in a focused state, the cornea-endothelium focusing-detection use receiving optics $18_1$ set at a position resulting from extending the part $14_1$ of the optical path of the optical system detects cornea endothelium reflected light that moves in front of the receiving optics $18_1$ as the imaging system 3 moves forward, thus detecting a focusing.

In more detail, the arrangement of the objective lens 15 and the (infrared-light transmitting and visible-light reflecting) half mirror 16 on the optical axis $14_1$ of the magnification-imaging optical system located symmetrically with the illumination optical axis 12 of the imaging system with the eye axis $2_1$ of the subject eye 1 interposed therebetween, and the arrangement of the field diaphragm 19 and the magnifying lens 20 and the like on the optical axis $14_2$ bent by the half mirror 16 are the same as in the first embodiment. Visible-light of the imaging-use slit light due to strobe light out of the magnified-image ray is totally reflected by an infrared-light transmitting and visible-light reflecting half mirror 21' disposed instead of the total-reflection mirror 21 of the first embodiment, so as to be incident on the image receiving surface (CCD photoreceptive surface) 22 of the TV camera 23 provided on a bent optical axis $14_3$. Meanwhile, infrared light of imaging-position (cornea endothelium focused position) detection use slit light will be incident on the cornea-endothelium focusing-detection use receiving optics $18_1$ located at an image-forming position of the cornea reflected image ray by the objective lens 15 on the extended optical path on the optical axis $14_1$, as in the first embodiment. Then, when the cornea endothelium image is formed on the image receiving surface 22 of the TV camera 23 by the objective lens 15 and the magnifying lens 20, slitted cornea endothelium reflected light for use of focusing detection will be incident on the photoreceptive area of the receiving optics $18_1$ as it has been well separated from adjacent, more-flared epithelium reflection with the slit aperture 17 elongated in the longitudinal direction of the cornea reflected image in front of the endothelium-focusing detection use receiving optics $18_1$ and as it has been narrowed in width by the slit aperture 7 located at a position where light emitted by the illumination lamp 4 is focused. Thus, the cornea endothelium reflected light can be detected by the receiving optics $18_1$ with high accuracy and reliability so that the optimum imaging position (focused position) for the apparatus can be detected. In this case, the cornea-endothelium focusing-detection use receiving optics $18_1$ can detect the focusing on the cornea endothelium easily and accurately by using a phototransistor as the receiving optics optimum for detection of focusing on cornea endothelium.

Also, out of the image rays of light magnified by the objective lens 15 and the magnifying lens 20, the slitted epithelium reflected light of infrared light passes the half mirror 21' so as to form an image on the epithelium-focusing detection use receiving optics $18_2$, where epithelium focusing is detected, and moves on the receiving optics $18_2$ as the imaging system 3 moves forward. In this case, by using a line sensor as the cornea-epithelium focusing-detection use receiving optics $18_2$, after the epithelium-focusing detection use receiving optics $18_2$ has detected an epithelium focusing, the position of epithelium reflected light that has moved from the position of epithelium-focusing detection at the time when an endothelium focusing is detected by the cornea-endothelium focusing-detection use receiving optics $18_1$ can be detected with high accuracy. Thus, the cornea thickness can be calculated from the resulting extent of movement. IT is noted that the imaging system 3 operates by the electric circuit as shown in FIG. 8.

Next, the operating procedure of the apparatus for obtaining images of cornea cells according to the present invention is described with reference to the block diagram as shown in FIG. 8 and the flow chart as shown in FIG. 9.

First, unshown power supply of the apparatus for obtaining images of cornea cells is turned on. The optical system, which is the imaging system 3, is manually aligned with the subject eye (alignment between center of pupil and center of TV image) and then moved forth toward the subject eye by driving the Z-axis with a Z-axis drive mechanism 35. During the forward movement of the imaging system 3, the endothelium-focusing detection use receiving optics $18_1$ senses cornea epithelium reflected light while the epithelium reflected light reaches the epithelium-focusing detection use receiving optics $18_2$ on another optical path. The imaging system 3 continues moving forth until the endothelium-focusing detection use receiving optics $18_1$ receives endothelium reflected light, where the cornea endothelium reflected light is detected by a slit-light reflection detector circuit 36. At this point, a strobe light emission control circuit 37 is actuated by a signal from the slit-light reflection detector circuit 36, causing the strobe discharge tube 8 to emit light. Then the reflected light from the eyeball surface 2 passes over the optical path of the magnification-imaging optical system, forming a magnified image of the subject part on the image receiving surface of the TV camera 23. An image signal of the magnified image of the cornea endothelium cells of the subject part from the TV camera 23 is written into a frame memory 32 by an image input/output control circuit 31. At the same time, the Z-axis drive mechanism 35 stops the imaging system 3 being moved forth by a signal from the image input/output control circuit 31, where the magnified image of the cornea endothelium cells is displayed on a monitor display 33.

On the other hand, when the receiving optics $18_1$ detects endothelium reflected light, the epithelium reflected light has moved after earlier reaching the receiving optics $18_2$. The position on the receiving optics $18_2$ of the epithelium reflected light that has moved is stored by a cornea thickness calculation circuit 38 via the slit-light reflection detector circuit 36. A cornea thickness in correspondence to the position on the receiving optics $18_2$ of the epithelium reflected light that has moved is calculated by the cornea thickness calculation circuit 38 and displayed on the monitor display 33 via the image input/output control circuit 31 together with the magnified image of the cornea endothelium cells, where the imaging process is ended. In this case, cornea thickness can be calculated advantageously by the absence of any movable part such as a rotary encoder. Also, the cornea thickness has been written in the frame memory 32 via the image input/output control circuit 31. Thus, both the magnified image of cornea endothelium cells and the cornea thickness can be printed out by a video printer 34 by reading them out from the frame memory 32 by the image input/output control circuit 31, as required, so that a video print of the subject eye may be attached to the medical sheet.

In the present embodiment, cornea endothelium reflected light out of cornea reflected light, even if weak, can be detected with high sensitivity by using receiving optics optimum for detection of the endothelium reflected light (e.g., phototransistor). Also, as for cornea epithelium reflected light, the extent of movement of epithelium reflected light at the time of detection of endothelium reflected light can be easily detected by using a line sensor, PSD, or the like capable of detecting the extent of movement of the epithelium reflected light in its moving direction, so that cornea thickness can be calculated easily and correctly by the cornea thickness calculation circuit.

According to the apparatus for obtaining images of cornea endothelium of the present invention as defined in claim 1, for obtaining an image of cornea endothelium cells of a subject eye, the state how the slit light is received by the focusing-detection use receiving optics mounted on the apparatus body is controlled so that cornea endothelium reflected light substantially weaker than cornea epithelium reflected light can be detected with reliability by the receiving optics. Moreover, the optimum imaging position for the apparatus can be detected easily and securely not only manually but also automatically for obtaining an image.

According to the present invention as defined in claim 2, for focusing detection by detecting cornea reflected light of a subject eye with focusing-detection use receiving optics, cornea endothelium reflected light can be well separated from proximate epithelium reflected light so that the focusing can be detected with reliability.

According to the present invention as defined in claim 3, for detection of a focusing by detecting cornea reflected light of a subject eye with focusing-detection use receiving optics, endothelium reflected light, which is too dark to detect, is brightened so that the difference in intensity between epithelium reflection and endothelium reflection is lessened. Thus, cornea endothelium reflected light can be detected with reliability.

According to the present invention as defined in claim 4, for detection of a focusing by detecting cornea reflected light of a subject eye with focusing-detection use receiving optics, endothelium reflected light, which is too dark to detect, is received by receiving optics which is enhanced in photoreceptive sensitivity, so that the difference in detection signal between epithelium reflection and endothelium reflection is lessened. Thus, cornea endothelium reflected light can be detected with reliability.

According to the present invention as defined in claim 5, for detection of a focusing by detecting cornea reflected light of a subject eye with focusing-detection use receiving optics, a slitted cornea reflected image can be received on its whole by the receiving optics without waste, so that detectability of the focusing-detection use receiving optics for cornea endothelium reflected light can be enhanced.

According to the present invention as defined in claim 6, the slit illumination can be changed in size in its widthwise direction depending on its purpose, by virtue of the slit illumination optical system having a detection-use slitted aperture independent of an imaging-use slitted aperture.

Thus, cornea endothelium reflected light can be detected with high accuracy so that an image can be obtained with a wider field of view.

According to the apparatus for obtaining images of cornea endothelium of the present invention as defined in claim 7, for observing or photographing a magnified image of cornea endothelium cells of an eyeball of a subject person, cornea endothelium focusing can be easily achieved in the imaging apparatus, whether manually or automatically, and moreover receiving optics optimum for detection of reflected light of cornea endothelium and cornea epithelium, respectively, can be used. Their respective photoreceptive optical paths may be modified to match the application without care for their influences on each other. Thus, the degree of freedom of design can be increased and photoreceptive function can be easily controlled. As a result, cornea endothelium can be detected with high accuracy and the epithelium position at the time when endothelium is detected can be detected with high accuracy.

According to the present invention as defined in claim 8, for calculating the cornea thickness in addition to obtaining a magnified image of cornea endothelium cells, there is no need of using any measuring means such as a mechanical encoder, so that the cornea thickness can be easily measured by an electronic measuring means.

What is claimed is:

1. An apparatus for obtaining images of cornea endothelium, which comprises an illumination system for illuminating through a slit an eyeball surface of a subject eye, a magnification-imaging optical system for forming a magnified image of a subject part based on slit illumination light with which the eyeball surface has been illuminated, focusing-detection use receiving optics set in such a position as to receive cornea endothelium reflected light and cornea epithelium reflected light of the slit light via at least an objective lens when a cornea endothelium image is formed on an imaging surface of the magnification-imaging optical system in a focused state, and a means for moving the apparatus body in the direction of the subject eye so that the apparatus body is brought to a cornea endothelium focused position, wherein the focusing-detection use receiving optics comprises a photoreceptor for receiving cornea endothelium reflected light and a photoreceptor for receiving cornea epithelium reflected light.

2. The apparatus for obtaining images of cornea endothelium according to claim 1, wherein said photoreceptor for receiving said cornea epithelium reflected light is a light receiving element capable of detecting an extent of movement of said epithelium reflected light in its moving direction, and wherein cornea thickness is calculated in correspondence to an epithelium-reflected-light received position on the photoreceptor for receiving said cornea epithelium reflected light at the time when said photoreceptor for receiving said cornea endothelium reflected light has detected said endothelium reflected light.

3. An apparatus for obtaining visual images of cornea endothelium, comprising illumination means for illuminating and for flashing an eyeball surface of a patient eye through a slit-shaped aperture;

magnification optical means for obtaining magnified, slit-shaped visual images of a subject portion of the eyeball surface via an objective lens based of the illumination means, a receiving optics for detecting a focusing of a cornea epithelium image and a cornea endothelium image obtained by the magnification optical means;

a video camera provided in front of the eye for monitoring the eyeball surface;

shifting means for moving an optical unit, which includes said illumination means, magnification optical means, receiving optics and video camera, toward the patient eye so as to obtain the focuses of the cornea epithelium and endothelium images; and image enhancing means for controlling detectability of the focusing of the cornea endothelium image by the receiving optics, wherein said receiving optics is arranged so that the cornea endothelium image focuses at a light receiving surface of the video camera when the focusing of the cornea endothelium image is detected by the receiving optics.

4. The apparatus for obtaining visual images of cornea endothelium according to claim 3, wherein said image enhancing means is a slitted aperture provided in front of the receiving optics so that a direction of the slit of the aperture is coincided with the longitudinal direction of the slit-shaped visual images of the magnification optical means.

5. The apparatus for obtaining visual images of cornea endothelium according to claim 3, wherein said image enhancing means is to increase an intensity of the illumination means based on a detection of the focusing of the cornea epithelium image by the receiving optics.

6. The apparatus for obtaining visual images of cornea endothelium according to claim 3, wherein said image enhancing means is to increase photoreception sensitivity of the receiving optics based on a detection of the focusing of the cornea epithelium image by the receiving optics.

7. The apparatus for obtaining visual images of cornea endothelium according to claim 3, wherein said image enhancing means is an optical means provided in front of the receiving optics for converging the longitudinal direction of the slit-shaped visual image.

8. The apparatus for obtaining visual images of cornea endothelium according to claim 3, wherein said image enhancing means is to provide a narrower first slit-shaped aperture for illuminating the eyeball surface and to provide a wider second slit-shaped aperture for flashing the eyeball surface.

9. An apparatus for obtaining visual images of cornea endothelium, comprising illumination means for illuminating and for flashing an eyeball surface of a patient eye through a slit-shaped aperture;

magnification optical means for obtaining magnified, slit-shaped visual images of a subject portion of the eyeball surface via an objective lens based of the illumination means;

a receiving optics for detecting a focusing of a cornea epithelium image and a cornea endothelium image obtained by the magnification optical means;

a video camera provided in front of the eye for monitoring the eyeball surface; and shifting means for moving an optical unit, which includes said illumination means, magnification optical means, receiving optics and video camera, toward the patient eye so as to obtain the focuses of the cornea epithelium and endothelium images, wherein a first receiving optics for detecting the focusing of the cornea endothelium image and a second receiving optics for detecting the focusing of the cornea epithelium image are provided; and said first receiving optics is arranged so that the cornea endothelium image focuses at a light receiving surface of the video camera when the focusing of the cornea endothelium image is detected by the first- receiving optics.

10. The apparatus for obtaining visual images of cornea endothelium according to claim 9, wherein said second receiving optics detects a displacement of the cornea epithelium image from a time of the focusing of the cornea epithelium image by the second receiving optics to a time of the focusing of the cornea endothelium image by the first receiving optics, thereby measuring a cornea thickness of the eye.

* * * * *